(12) United States Patent
Dempster

(10) Patent No.: US 12,111,300 B2
(45) Date of Patent: *Oct. 8, 2024

(54) CONTINUOUS WAVE SONIC ANALYZER

(71) Applicant: Evoqua Water Technologies LLC, Pittsburgh, PA (US)

(72) Inventor: Philip Tinsley Dempster, Concord, CA (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/632,233

(22) PCT Filed: Jul. 31, 2020

(86) PCT No.: PCT/US2020/044519
§ 371 (c)(1),
(2) Date: Feb. 1, 2022

(87) PCT Pub. No.: WO2021/022168
PCT Pub. Date: Feb. 4, 2021

(65) Prior Publication Data
US 2022/0268736 A1 Aug. 25, 2022

(51) Int. Cl.
*G01N 33/00* (2006.01)
*G01N 29/024* (2006.01)
(Continued)

(52) U.S. Cl.
CPC ....... *G01N 33/0039* (2013.01); *G01N 29/024* (2013.01); *G01N 29/326* (2013.01);
(Continued)

(58) Field of Classification Search
CPC ........... G01N 33/0039; G01N 33/0004; G01N 29/024; G01N 29/326; G01N 29/345;
(Continued)

(56) References Cited

U.S. PATENT DOCUMENTS 3,895,630 A 7/1975 Bachman
4,155,246 A 5/1979 Dempster et al.
(Continued)

FOREIGN PATENT DOCUMENTS

CN 203148896 U 8/2013
JP 2003279549 A 10/2003
(Continued)

OTHER PUBLICATIONS

International Search Report in corresponding PCT/US20/44519, dated Dec. 18, 2020.
(Continued)

*Primary Examiner* — Suman K Nath
(74) *Attorney, Agent, or Firm* — Evoqua Water Technologies LLC

(57) ABSTRACT

A gas analyzer uses continuous sonic signals through a conduit to determine the composition of a gas in the conduit. A transmitting transducer drives sonic signals at a fixed frequency and a second transducer receives the sonic signals. The phase shift between two signals corresponds to the speed of sound through the gas and is related to the composition of the gas. The electronic versions of these signals are processed by lowering, or dividing, the fixed frequency which expands the range of phase shift measurement and allows the determination of an expanded range for the gas composition. In an ozone generation system, the gas analyzer is highly suitable for determining the composition of gases derived from air as a gas of known composition and a calibration point.

23 Claims, 5 Drawing Sheets

(51) Int. Cl.
  *G01N 29/32* (2006.01)
  *G01N 29/34* (2006.01)
(52) U.S. Cl.
  CPC ......... *G01N 29/345* (2013.01); *G01N 29/348* (2013.01); *G01N 33/0004* (2013.01); *G01N 2291/021* (2013.01); *G01N 2291/0215* (2013.01); *G01N 2291/02809* (2013.01); *G01N 2291/02881* (2013.01); *G01N 2291/102* (2013.01)
(58) Field of Classification Search
  CPC .... G01N 29/348; G01N 29/36; G01N 29/222; G01N 2291/021; G01N 2291/0215; G01N 2291/02809; G01N 2291/02881; G01N 2291/102; G01N 2291/048; G01H 5/00; Y02A 50/20
  See application file for complete search history.

(56) References Cited

U.S. PATENT DOCUMENTS

| | | | |
|---|---|---|---|
| 5,351,522 | A | 10/1994 | Lura |
| 5,644,070 | A | 7/1997 | Gibboney et al. |
| 6,202,468 | B1 | 3/2001 | Dempster et al. |
| 6,378,372 | B1 | 4/2002 | Karr |
| 6,520,001 | B2 | 2/2003 | Dempster et al. |
| 6,520,221 | B2 * | 2/2003 | Gatteschi .............. B65B 39/004 141/351 |
| 2002/0137227 | A1 | 9/2002 | Weckstrom |
| 2007/0245802 | A1 | 10/2007 | Austerlitz et al. |
| 2013/0165806 | A1 * | 6/2013 | Wondka .............. A61B 5/0836 600/532 |
| 2013/0199265 | A1 * | 8/2013 | Bernat ................ G01M 15/102 73/23.21 |
| 2014/0194703 | A1 * | 7/2014 | Wondka ................ G16H 10/40 600/301 |
| 2017/0197056 | A1 | 7/2017 | Van Schalkwyk et al. |
| 2019/0094195 | A1 | 3/2019 | Gentner |

FOREIGN PATENT DOCUMENTS

| | | |
|---|---|---|
| JP | 2005043091 A | 2/2005 |
| JP | 2007304017 A | 11/2007 |
| JP | 2008256485 A | 10/2008 |
| WO | 2004/079306 A1 | 10/2004 |
| WO | 2017/180933 A1 | 10/2017 |

OTHER PUBLICATIONS

Filipas, Alin, "Extended European Search Report", European Patent Application No. 20846066.7, mailed Jul. 19, 2023, 8 pages.

Unknown, "Search Report", Taiwanese Patent Application No. 109127217, mailed Nov. 16, 2023, 27 pages.

Shimizu, Yasunori, "Notice of Reasons for Refusal", Japanese Patent Application No. 2022-504720, mailed Jan. 9, 2024, 14 pages.

* cited by examiner

CONTINUOUS WAVE SONIC ANALYZER

BACKGROUND OF THE INVENTION

This invention relates to gas composition analyzers and, more particularly, to gas composition analyzers for the generation of ozone. Ozone is a highly active form of oxygen often used for disinfection and water treatment. Due to its characteristics, ozone is typically generated on site and at the time of use.

Ozone may be generated in many ways, one of which is by the ionization of oxygen using electrical discharge to create a plasma. Ozone when generated by electrical discharge has a concentration that depends on many factors, including but not exclusively, the composition of the feed gas, the flow rate of feed gas, the temperature of ozone generation cell, the dimensions and materials of the cell, and the electrical power used to generate the plasma. The plurality of factors affecting ozone production makes it very difficult to predict ozone production with any precision. If control or knowledge of ozone production is desired, it is necessary or desirable to monitor ozone production. An analyzer on site is required for this purpose.

There are several different techniques available to an analyzer for measuring the concentration of ozone in a gas. These include using the absorption of UV light in the gas, such as found in the products from Oxidation Technologies, LLC of Inwood, Iowa and Teledyne API of San Diego, California. This technique is effective but production costs are high. Furthermore, no information on the composition of the feed gas to the ozone-generating cell is obtained. Knowledge of the feed gas composition, which may consist of dry air with an increased concentration of oxygen, is desirable. Electrical discharge ozone generators operate more efficiently with a high proportion of oxygen. Therefore, oxygen concentrators are sometimes used to increase oxygen from 20.9% (ambient air) to values above 90%. For an electrical discharge ozone generator, the presence of small amounts of nitrogen in the feed gas appears to enhance efficiency significantly. But it is possible to remove too much nitrogen from the feed gas such that efficiency of the cell is reduced. In such oxygen-concentrated air, the principal components are nitrogen, oxygen, and a small amount of argon. By complementation, the concentration of nitrogen can be estimated from the concentration of oxygen.

Use of the speed of sound to estimate the concentration of ozone in a gas is described in U.S. Pat. No. 5,644,070 (Gibboney). With the temperature of the feed gas, the speed of sound of the feed gas, the temperature of the gas as it emerges from an ozone generator, and the speed of sound of the gas as it emerges from the ozone generator measured or known, the speed of a sound pulse in the gas is determined by measuring delay over a known path length. The four measured or known variables are used to estimate the concentration of ozone. However, with a resonant transducer a pulse necessarily consists of multiple cycles which make the precise determination of the arrival of a pulse of sound difficult; it is difficult to ascertain when a pulse begins and when it ends. A further disadvantage is that the described system is complex. The sound pulses require relatively long measurement paths and hence conduits with relatively high volume which increases the required sample gas volumes. A scavenging pump, which is costly, is used to move either the feed gas to the ozone generation cell or the output gas from the cell. This complicates the measurement system. The pump must be made of materials that do not deteriorate over time in the presence of high concentrations of corrosive ozone.

The speed of sound in a continuous sonic wave is used to help determine the concentrations of two gases, neither of them ozone. U.S. Pat. Nos. 6,202,468 and 6,520,001 by the present inventor describe a system in which that technique is combined with another. Two distinct and unrelated physical parameters, paramagnetism and the speed of sound, are measured to determine the concentration of both oxygen and carbon dioxide in respiratory gas. In this case, the use of sound alone cannot determine the concentration of either gas.

Hence there is a need for a low cost analyzer with the capability to measure both the concentration of oxygen in feed gas to an ozone generating cell and the concentration of ozone in the cell output. Such an instrument may be used for the assessment of generated ozone and for process control. For example, oxygen concentration may be adjusted, based upon instrument output, so as to maintain a desired concentration of ozone, and cell power may be controlled, based instrument output to maintain a desired concentration of ozone. A single low-cost analyzer to handle both of these functions would be both convenient and economical. It is an object of the present invention to perform both functions in a single, reliable, low-cost instrument.

BRIEF SUMMARY OF THE INVENTION

The present invention provides for an analyzer for one or more gases derived from a first gas of known composition and speed of sound, each derived gas having a concentration of a component changed. The analyzer has: a first transducer which drives continuous sound waves responsive to a fixed frequency signal source; a conduit acoustically connected to the first transducer and selectively receiving and holding samples of the first gas and one or more derived gases; a second transducer acoustically connected to the conduit opposite the first transducer unit, the second transducer which receives sound waves from the first transducer through the conduit and generates second transducer signals responsive to the received sound waves; a processing unit which receives the fixed frequency signal source signals and the second transducer signals, and which determines a relative phase shift between the frequency source signals and second transducer signals for a gas sample in the conduit, the relative phase shift corresponding to a difference of speed of sound in one gas sample relative to another gas sample, the processing unit including circuitry lowering the frequency of the received fixed frequency source signals and second transducer signals to expand the range of measurement of the relative phase shift; and a calculating unit which determines from the first gas of known composition the speed of sound of the one or more gases derived from the first gas, and which calculates the composition of a sample of one or more derived gases from the first gas as a reference.

The present invention also provides for a method of operating an analyzer for one or more gases derived from a first gas of known composition and speed of sound, each derived gas having a concentration of a component changed. The method has the steps of: driving continuous sound waves with a first transducer in response to fixed frequency electrical signals through a conduit holding a sample of the first gas or one or more derived gases at a time; receiving the sound waves driven through the conduit by a second transducer and generating electrical signals in response to the received sound waves, a relative phase shift between the received sound wave signals and the driven sound wave signals corresponding to a relative speed of sound in the gas samples; processing the fixed frequency electrical signals and the electrical signals generated signals in response to the received sound waves at a lowered frequency to expand the range of measurement of the relative phase shift; determining the speed of sound of the first gas of known composition and one or more gases derived from the first gas in the expanded range from the relative phase shift of gas samples of the first gas of known composition and one or more gases derived from the first gas in the conduit; and calculating a composition of a sample of one or more gases derived from the first gas as a reference.

The present invention further provides for a method of determining the composition of one or more gases derived from a first gas of known composition and speed of sound. The method has the steps of: driving continuous sonic waves through a conduit at a fixed frequency, a phase difference between sonic waves entering the conduit and leaving the conduit corresponding to a speed of sound of a gas in the conduit; processing electronic signals corresponding to the continuous sonic waves entering the conduit and leaving the conduit at a lowered frequency to expand the range of measurement of the phase shift; changing the gas in the conduit among the first gas and the one or more derived gases; determining the speed of sound of the first gas of known composition and the one or more gases derived from the first gas in the expanded range from a relative phase shift of gases of the first gas of known composition and the one or more derived gases, the relative phase shift corresponding to a difference of speed of sound in one gas sample relative to another gas sample; and calculating a composition of the one or more derived gases from the first gas as a reference.

Other objects, features, and advantages of the present invention will become apparent upon consideration of the following detailed description and the accompanying drawings, in which like reference designations represent like features throughout the figures.

DETAILED DESCRIPTION OF THE INVENTION

As described below, the present invention provides for the measurement of ozone concentration with high resolution and precision. The ozone concentration is measured relatively independently of the oxygen concentration in the feed gas and independently of temperature. The construction of the analyzer is also simple and low-cost.

Figure 1:
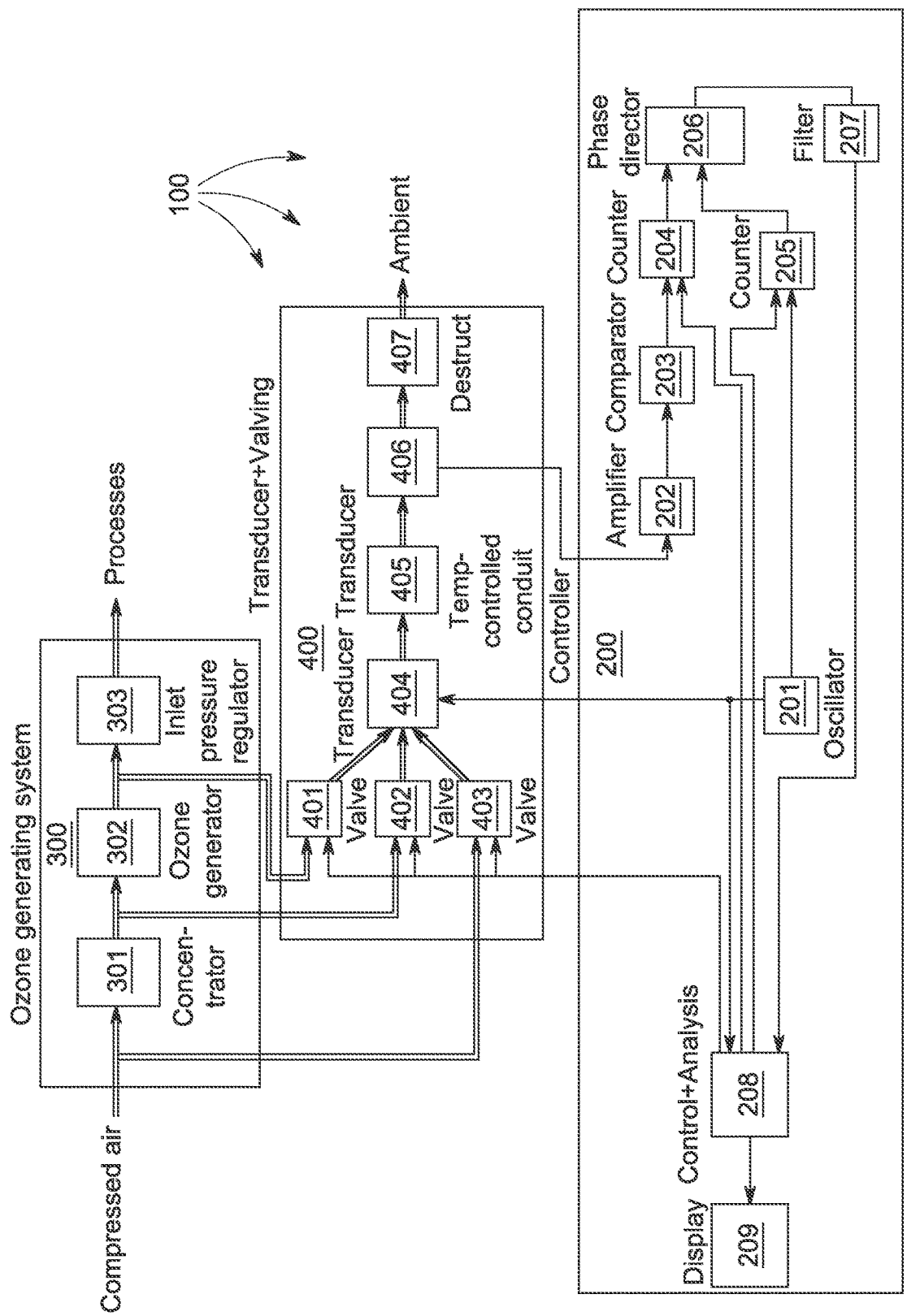
FIG. 1 shows the general organization of an analyzer in an ozone generation system according to one embodiment of the present invention.

FIG. 1 shows a generalized view of a portion of an ozone generation system with a continuous sonic wave analyzer unit according to one embodiment of the present invention. It should be noted that drawing is representational and the elements of the drawing are not drawn to scale. The system has an ozone generation block 300 and a continuous sonic wave analyzer unit 100 which is formed by a transducer/valve block 400 and controller/analysis block 200. The ozone generation block 300 receives compressed air from a source (not shown) and delivers generated gas including ozone to a process, i.e., the particular application of the ozone. The compressed air (gas flow is shown by the broadened arrows in the drawing) is received by a concentrator 301 which increases the percentage of oxygen in the resulting gas. The gas from the concentrator 301, which may be a swing pressure absorption device, is passed to an ozone generator 302, typically an electrical discharge cell. The gas output from the ozone generator 302 is sent to an inlet pressure regulator 303 which controls the pressure of the gas and ozone sent to the process, the application using the generated ozone.

The analyzer unit 100 determines the relative speeds of sound of gas at different locations of the ozone generation block 300 and comprises a transducer/valve block 400 and a controller/analysis block 200. The transducer/valve block 400 processes samples of gas from the different locations and the controller/analysis block 200 controls the operations of the transducer/valve block 400 and analyzes the output from the transducer/valve block 400. The transducer/valve block 400 has a first input valve 403 which receives the compressed air from the source to the concentrator 301; a second input valve 402 which receives the output gas from the concentrator 301 to the ozone generator 302; and a third input valve 401 which receives the output gas from the ozone generator 302 to the inlet pressure regulator 303. The outputs of the valves 401-403 are connected to a first transducer unit 404 which has its output connected to a gas conduit 405 which in turn is connected to a second transducer unit 406. The transducer unit 404 transmits sound in a continuous wave through the conduit 405 to the receiving transducer unit 406 to determine the relative speed of sound through the gas in the conduit 405 (and transmitting transducer units 404 and receiving transducer unit 406). The gas output of the receiving transducer unit 406 is connected to a destruct unit 407 which eliminates the ozone in the sampled gas before releasing the gas into the ambient air.

In general, a reference phase reading is taken for a first gas of known composition (usually ambient air) and then unknown second and third gases are introduced, producing corresponding changes of phase shift, and from these changes of phase shift and the known speed of sound of the first gas, the speed of sound of the second and third gases are computed.

Ozone is highly corrosive and care is taken in the selection of the components in contact with ozone. The transducer units 404 and 406 are formed from aluminum which forms a tough coating of aluminum oxide and the conduit 405 is formed from polytetrafluoroethylene (PTFE) tubing which resists ozone. The conduit 405 is also temperature-controlled to maintain the temperature of the gas in the conduit at a desired temperature and has a relatively large thermal mass to stabilize the conduit temperature. The length L of conduit 405 is preferably long enough to give good sensitivity to the device and to prevent artifacts due to standing waves, yet short enough to be low in volume, convenient to fabricate, and unambiguous with respect to measuring phase shift. From the point of view of sensitivity and standing waves, a preferable pathlength L may be about 24 wavelengths, although other pathlengths may be used. But a pathlength of 24 wavelengths may result in ambiguous readings due to excessive change of phase shift as speed of sound varies with changing gas composition. For example, phase shift due to replacing air with oxygen would be about 0.9 wavelengths. Phase shift due to replacing air with a mixture of ozone and oxygen may be as much as two wavelengths. A method to mitigate this problem using frequency division is a feature of the invention and is described below. The method allows choice of pathlength based on a desired compromise of the mentioned factors without concern for ambiguous results from a phase detector.

The controller block 200 of the analyzer unit 100 has an oscillator unit 201 which drives the first transducer unit 404 in the transducer/valve block 400. A first counter 205 receives a control signal from the control unit 208 and a driving signal from the oscillator 201. An amplifier 202 in the controller block 200 receives the electrical output of the second transducer unit 406. The output of the amplifier 202 is received by a comparator 203 which shapes the amplified signals to square waves. The comparator output is sent to a second counter 204 which counter 204 also receives a control signal from the control unit 208. The outputs of both counters 204 and 205 are sent to a phase detector 206 and the phase detector output is passed through a low-pass filter 207 to the control unit 208.

The present invention uses the speed of sound in a gas to determine the concentration of ozone in the gas. Sound in ozone is considerably slower than sound in oxygen due to higher molecular weight of ozone relative to oxygen. Likewise, sound in oxygen is slower than sound in air, due to higher average molecular weight of oxygen relative to air. For a gas which has only two components and if the speed of sound of each component is distinct from the other, the measured speed of sound though the gas is characterized by the proportions of the two components. This is true even if the components themselves comprise mixtures of more than one gas. Discussion of this may be found in the previously cited U.S. Pat. Nos. 6,202,468 and 6,520,001.

Figure 2:
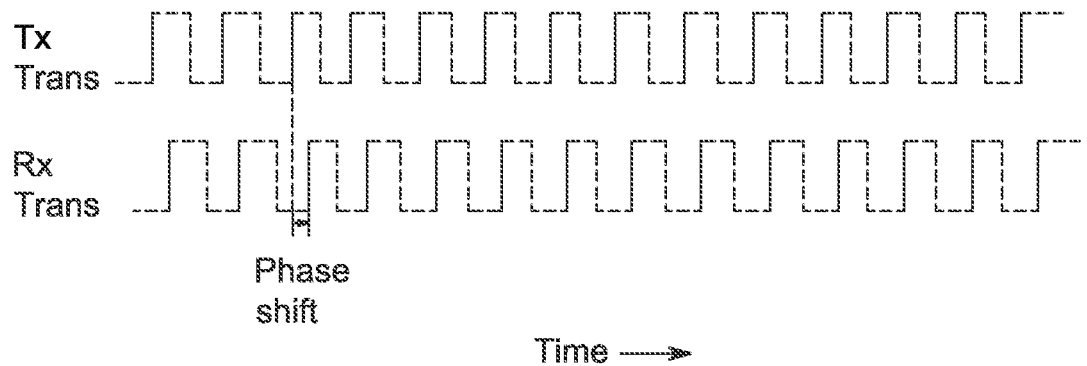
FIG. 2 represents fixed frequency signals to the source transducer and the signals from the receiving transducer of the analyzer unit of FIG. 1.

The speed of sound in a gas is found by the known characteristics of the first gas introduced, and the corresponding change in phase shift which the continuous sonic wave originating from the source transducer undergoes as the wave travels to the receiving transducer with subsequent gases. FIG. 2 shows the sonic wave train from the transmitting transducer 404 as a series of square waves indicating the digital nature of the signals and the circuitry processing the signals. Analog signals and circuitry may also be used. The rising edges of the waves shown as solid vertical bars to serve as reference points to aid the reader's understanding. Likewise, another series of square waves received by the second transducer 405 is illustrated with solid bar rising edge of each sonic waves received by the second transducer 405. An arrow indicates the phase shift reflecting the time interval for a particular wave front to travel from the source transducer 404 to the receiving transducer 405. It should be evident that the longer the time interval, or the slower the speed of the sonic waves through the gas medium, the greater the phase shift.

The phase shift should be kept within a restricted range due to the nature of the continuous wave to determine the amount of shift with certainty. For example, it is difficult to determine whether a phase shift is x or x+i*360°, where i is an integer. So in this example only phase shifts of less than 360° should be undertaken. But this severely limits the range of speeds which can be determined. It should be noted that limited phase range is also dependent upon the circuits used to determine the phase shift which may limit the phase shift even more, such as from 0° to 180°. In any case, the present invention expands the range of speeds which can be determined as explained below.

Figure 3:
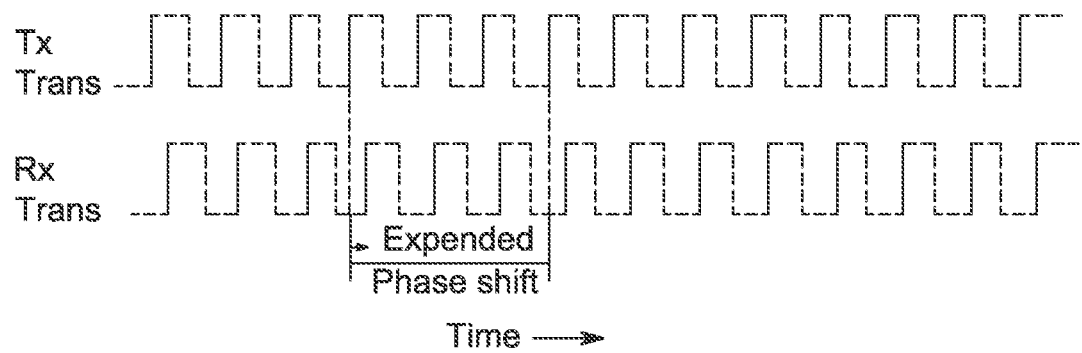
FIG. 3 illustrates how lowered frequency of the FIG. 2 signals to the source transducer and from the receiving transducer of the analyzer unit expands the range of measurement of phase shift, according to an embodiment of the present invention.

While the source transducer is driven at a fixed frequency, the frequency of the source signals is lowered for processing. FIG. 3 represents an exemplary lowering of frequency of 66% or stated differently, dividing the frequency by 3, by the elimination of 2 out of 3 vertical bars. Elimination is indicated by the replacement of a solid bar (representing a rising edge) with a barred bar. With the lowering of the frequency, the phase shift range (and hence the sound speed range) which can be determined is accordingly expanded. That is, assuming a phase limitation of 0-360°, the frequency lowering by 3 allows the phase shift range to be expanded by 3 so that the range is expanded to 0-1080°. Frequency reduction proportionately increases the range of phase shift measurement and allows high precision measurement without the shortcomings of a short path length conduit. A short path length may typically introduce signal artifact due to standing waves or residues of standing waves in the conduit. Frequency reduction avoids these problems.

Figure 4A:
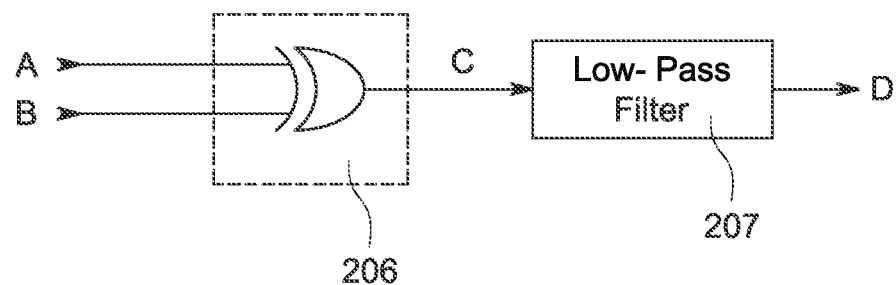
FIG. 4A shows a simplified circuit for the phase shift detector in FIG. 1.
Figure 4B:
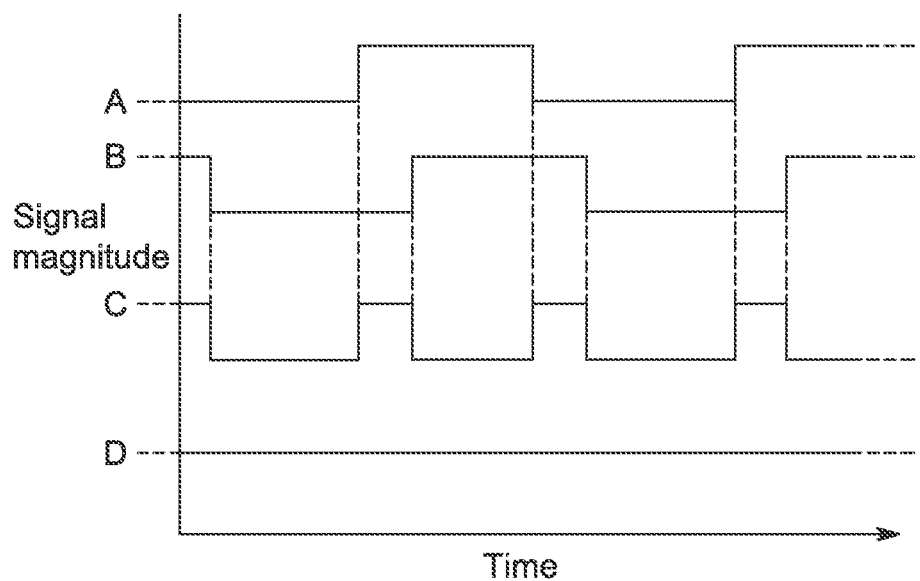
FIG. 4B shows exemplary transmitting transducer signals and receiving transducer signals, the resulting output signal from the FIG. 4A phase shift detector, and resulting signal after the phase detector output has passed through a low-pass filter of FIG. 1.

A simple representation of the electronic circuitry in FIG. 4A demonstrates the measurement of phase shifts as previously described. Two square wave data streams, A representing the signals for the transmitting transducer (404 in FIG. 1) and B representing the signals for the receiving transducer (406 in FIG. 1), are input to an Exclusive-OR logic gate (part of the circuitry of phase detector 206). The output C of the gate is input to a low-pass filter (207 in FIG. 1) which has an output D. FIG. 4B shows the relationship of the A and B signals, and the output C signal of the Exclusive-OR gate. Besides an Exclusive-OR gate, an Exclusive-NOR gate may also used for the phase detector 206.

Figure 4C:
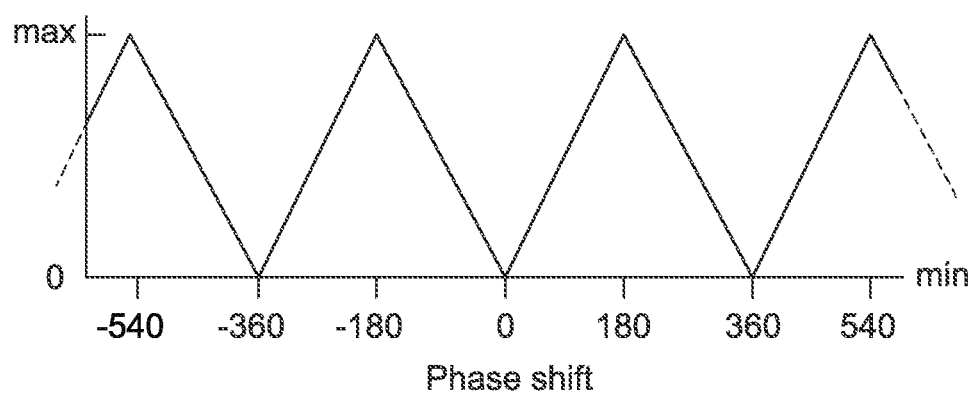
FIG. 4C shows the output of the low-pass filter for different phase shifts.

FIG. 4B also shows the output D signal of the low-pass filter 207 by which the mostly varying signal of the Exclusive-OR gate is filtered to reflect the "average" value of the output signal. For example, if the A and B signals are completely out of phase with each other (i.e., a phase difference of 180°), then the filtered phase difference, or phase shift, signal, the output D, is a maximum; if the A and B signals are completely in phase with each other (i.e., a phase difference of 0°), then the output D is a minimum, i.e., zero. If the A and B signals are "half" out of phase, or half in phase, i.e., the phase difference is 90°, and the output D is halfway between the maximum and the minimum, i.e., one-half the maximum. FIG. 4C illustrates how this phase detector value, the output D, varies with the phase difference between signals A and B. Here the phase differences are shown as values less than −540° to greater than 540°. The minus and positive values indicate whether the A, or the B, signals leads the B, or the A, signals. As described above, the A signals lag the B signals. FIG. 4C further graphically shows why the phase shift should be within a restricted range. In this illustration the phase shift should be restricted to a range of 180° to avoid ambiguity in determining the phase shift from an output D value.

Figure 4D:
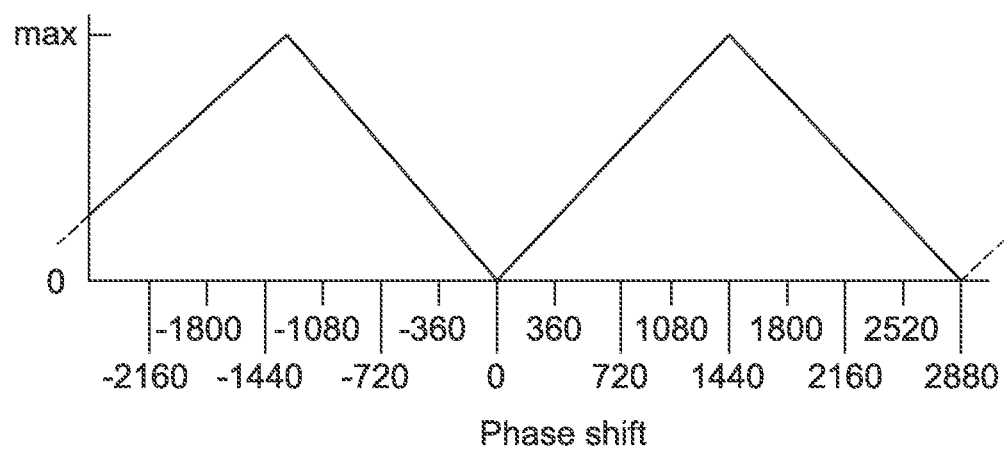
FIG. 4D shows the output of the low-pass filter for different phase shifts for the baseline adjustment.

When the frequency of A and B signals is lowered, the output D of the low-pass filter 207 is changed. In the example of FIG. 4D counters (205 and 204 in FIG. 1) are inserted into the data streams of the A and B digital signals to lower the frequency by a divisor of 8 (N=8 for the counters). The divisor N is arbitrary and chosen to suit the convenience of the designer. The output D is correspondingly spread. Instead of a cycle of 360° (as shown in FIG. 4C), the output D cycle is 8 times larger, 2880°, i.e., the output D signal repeats every 2880°. In this example, the phase shift is expanded to a range of 1440°, one-half of 2880°. This is a far larger range than 180° restriction without the frequency-lowered signals.

Thus an expanded range for the filtered phase shift signal, the output D, is easily implemented by digital counters, e.g., counters 205 and 204 in FIG. 1. Using the example above where N=8, the counter for the A signal data stream is set to zero and then started. When the A counter reaches a particular value, say 1, then the counter for the B signal data stream is set to zero and started. This assures a non-negative starting value for the phase detector where N=8. The output D is thus between zero and 0.125 (assuming the maximum output D is 1.0). The amount 0.125 is ⅛. If the phase difference between the A and B signals, due to a different gas sample in the conduit 405 (see FIG. 1), now increases, the output D also increases linearly over a range of 1260° (1440°*(1−(⅛))) up to the maximum value. Again it should be noted that the counter divisor N and corresponding expansion of the phase shift measurement is arbitrary.

The two frequency-lowering counters 205 and 204 introduce phase uncertainty. In the above case of divide-by-8, there are 8 possible phase relationships depending on the counting relationship of the two counters. If the first counter 205 has count N, then the second counter 204 may have any of (N+n) mod 8 values, where n equal any integer in the range 0 to 7. If every waveform is properly counted, that relationship is maintained indefinitely. Control of the number n provides the opportunity to adjust the baseline with a resolution of ⅛ of full scale. In example immediately above, the receiving transducer signal initially starts in the "2$^{nd}$" relationship with the transmitting transducer signal, (N+n) mod 8=1. By controlling n so that (N+n) mod 8=0, the baseline is adjusted so the phase measurement range is expanded to its maximum extent and the determination of gas composition is maximized, and is a feature of the present invention.

For the phase shift detection described above, the electronic circuitry of the controller block 200 of the analyzer unit 100 is implemented by digital circuits, according to an embodiment of the present invention. The oscillator block 201 generates signals at a fixed frequency. In this embodiment the frequency is 40 KHz. The oscillator block signal drives the transmitting transducer 404 and is divided in frequency by 8, or stated differently, the counter 205 steps down, or lowers, the signal frequency by a factor of 8. The output of the counter 205 is received by the phase detector block 206.

The output of the receiving transducer 206 is processed into square waves by comparative logic (block 203) after being amplified by the amplifier 202. The counter 204 divides the signal frequency by 8. The output of the counter 204 is also received by the phase detector block 206. Through the operation of an Exclusive-OR or an Exclusive-NOR gate, the phase detector 206 output varies between the two power levels of the logic gate, say, 0 and 5 volts, for example. The low-pass filter 207 eliminates the AC component of the output signal.

Control of the continuous sonic wave analyzer unit 100 is performed by the control unit 208 in the controller/analysis block 200. In this embodiment the control unit 208 is basically a programmed microprocessor or microcontroller with memory. Among other contents, the memory stores values from the filtered phase detector 206. Control lines from the unit 208 extend to each of the valves 401-403 and the counters 205 and 204. The unit 208 also receives phase shift values from the output of the low-pass filter 207. A display 209 is connected to the control unit 208 provides a visual interface for the operations of the analyzer unit 100.

Under the control unit 208, the analyzer unit 100 with an expanded phase shift range determines the speed of sound in multiple gases and the composition of gases. The following description refers to the production of ozone and to the FIG. 1 system, but the analyzer unit should not be considered so limited. Briefly stated, ambient air, is introduced into the conduit and the valves closed. The output of the filtered phase detector is read and recorded for ambient air. Then feed gas, oxygen-enriched air, is introduced into the conduit and the valves closed. The output of the filtered phase detector is read and recorded for the feed gas. Finally ozone-bearing gas is introduced into the conduit and the valves closed. The output of the filtered phase detector is read and recorded for ozone-bearing gas.

Figure 5:
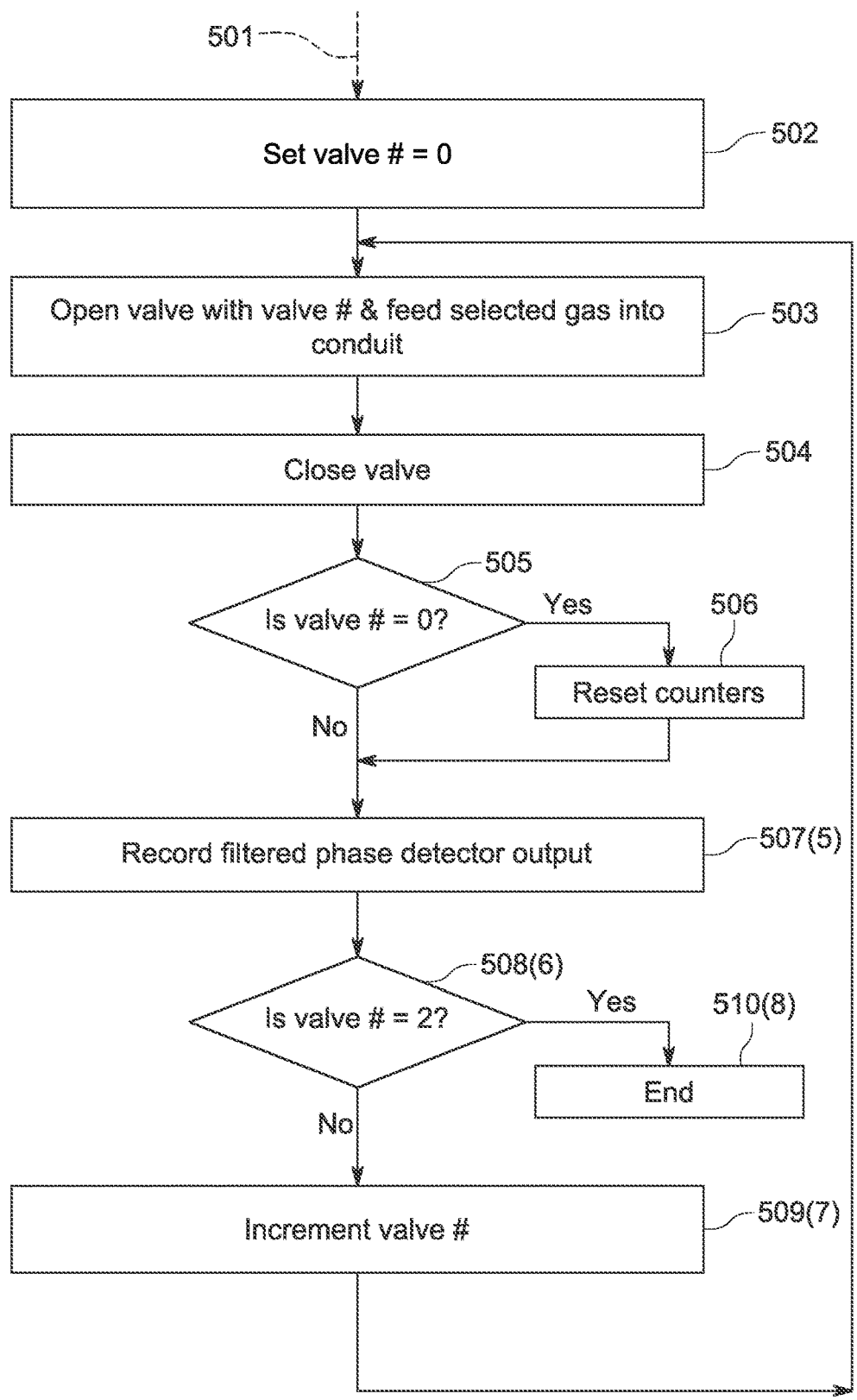
FIG. 5 shows a flow chart of operations of the analyzer unit in the operation of ozone generation system according to an embodiment of the present invention.

FIG. 5 shows a process flow of the operation described immediately above. The steps of the process flow are generalized in that the gases are labeled A, B and to indicate that more gases derived from the initial gas may be included in this process flow. After the system is initialized as represented by the dotted arrow 501, step 502 initializes an index Valve # to zero. Then the valve indicated by Valve # is opened and the gas selected by the opened valve is fed into the conduit by step 503. (In the FIG. 1 ozone generation system, index Valve #=0 corresponds to value 403, index Valve #=1 corresponds to value 402, and index Valve #=2 corresponds to value 401). Step 504 closes the valve. Step 505 tests whether the index Valve # is zero or not. If the index is 0, the counters are reset and the output value of the filtered phase detector is read and recorded by step 507. If the index is not 0, the test of step 505 moves to step 507. After step 507 the index Valve # is tested whether it is equal to 2 by step 508. If not, then step 509 increments the index Valve # by 1 and the process returns to step 503. The steps are repeated until index Valve # is equal to 2 and the process ends by step 510.

From the recorded phase shift values, the control unit 208 analyzes the data to determine the speed of sound and composition of the gases. A comparative technique is used. With the speed of sound and composition of the first gas already known, dehumidified ambient air is used as a reference to determine the speed of sound and composition of gases derived from the first gas, the ambient air. In particular, the speed of sound of the dehumidified ambient air at the set temperature of the temperature-controlled conduit is known and used as a reference to calculate the speed of sound of the second gas, oxygen-enriched feed gas, and of the third gas, the enriched air bearing ozone, from the measured phase shifts.

The gases are processed in the order of decreasing speed of sound, i.e., ambient air, ambient air enriched with oxygen, and oxygen-enriched air bearing converted ozone. The enriched air is derived from the ambient air and the ozone-being air is derived from the enriched air. Each gas is more dense than the gas preceding it, and the speed of sound decreases relative to the speed in previous gas(es). The first gas (dry ambient air) is treated as a reference gas because its composition is known. Its speed of sound at a given temperature is also known. While it is possible to allow the temperature to vary in the manner described in the previously described U.S. Pat. No. 5,644,070 (Gibboney), it is preferable that the temperature of the gases be maintained at a set temperature. The temperature—controlled gas conduits, such as illustrated in FIG. 1, have been found effective at maintaining gases at a set temperature. Thus in calculating the speed of sound in the oxygen-enriched air and ozone-bearing air, it is assumed that all gases have the same temperature. The addition of thermal mass or control of the environmental temperature is desirable in order to minimize error. With the speed of sound being the greatest in the reference first gas, the baseline may be adjusted as described earlier so that the phase shift ranges of the oxygen-enriched air and ozone-bearing air are expanded to accommodate the compositions of those gases.

The sound propagated in oxygen-enriched air arrives at the second transducer a little later than for ambient air. The additional delay is measured by the phase shift in combination with the known conduit length L between the first and second transducers. This allows determination of the speed of sound of the oxygen-enriched air as a function of speed of sound of ambient air and the additional phase shift. As described above, there is a direct relationship between the phase shift and delay. In particular, with L=length of sound path, $S0$=known speed of sound in ambient air, then delay $D0$ of the ambient air is $D0=(L/S0)$, a known quantity. The delay $D1$ of oxygen-enriched air is $D-+Dx$, where $Dx$ is the additional delay due to slower speed of sound in the oxygen-enriched air and is known from the additional phase shift for the oxygen-enriched air. Hence $S1=L/D1=L/(D0+Dx)$. With L, $D0$ and $Dx$ known, Si is determined.

The speed of sound of the ozone-bearing air is measured in the same fashion. With $S0$=known speed of sound in the ambient air, $S1$=speed of sound in the oxygen-enriched air, and $S2$=speed of sound in the ozone-bearing air. The delay $D2$ of ozone-bearing air is $D0+Dz$, where $Dz$ is the additional delay due to slower speed of sound in the ozone-bearing air and is known from the additional phase shift for the ozone-bearing air. Hence $S2=L/D2=L/(D0+Dz)$. With L, $D0$ and $Dz$ known, $S2$ is determined.

The speed of sound $S0$ of ambient air, which has an oxygen composition of 20.9%, is known and the speed of sound of 100% oxygen is also known. The measured speed of sound $S1$ of the oxygen-enriched gas should fall between the two known speed of sound values as a proportion of oxygen representing a mixture of the two gases, ambient air and 100% oxygen. This proportion may be calculated: proportion $O_2=(S1-S0)/(S_{ox}-S0)$ where $S_{ox}$ is the speed of sound in 100% oxygen gas. This discussion avoids many complex factors. The theoretical speed of sound in a gas can calculated from many models, which in turn have many factors, including Boltzmann's constant, temperature, mass of a molecule, and adiabatic constant (which is not the same for all gases under discussion), discourage theoretical certainty. Fortunately, certain assumptions of linearity yield reasonable approximations in the regions of interest. Empirical scaling yields good results.

Hence it has been found that: percentage $O_2=79.1\times$(proportion $O_2\times O_2\text{scale})+20.9$ is a very good approximation. Because this model is approximate and small variations will occur in the real world, the scaling factor $O_2$scale, near unity, is used to proportion $O_2$.

Similarly, for the ozone-bearing air: proportion $O_3=O_3\text{scale}\times3.329\times(S1-S2)/$(calculated speed of sound in pure ozone). The speed of sound in pure ozone is calculated because there is likely no way of empirically determining that speed of sound at ordinary temperatures due to the explosively unstable nature of such a gas. The number used is by calculation based upon molecular weight, temperature, and adiabatic constant. $O_3$scale is an empirical scale adjustment having a value of near unity.

To determine the concentration of ozone in terms of amount of ozone per cubic centimeter the following equation may be used: grams of ozone per cm$^3$=proportion $O_3\times2142.8571$.

Correction factors arise from complexities in the measurement of gas composition. The production of ozone may not depend on dilution of one gas by another. For example, if 1 mole of oxygen passes through an electrical discharge ozone cell and 10% of the $O_2$ is converted to $O_3$, the emerging ozone from the cell is 0.666 . . . mole due to the reduction in the number of molecules from the conversion from $O_2$ to $O_3$. The total oxygen emerging is 0.9 mole. Hence the total emerging gas is 0.9666 . . . mole and the molar percentage $O_3$ is 6.9%. But the speed of sound still has a 1-to-1 relationship to the ozone concentration.

If the gas entering the discharge cell consists of more than one component, the situation is similar. For example, if the gas entering the cell is 90% $O_2$ and 10% $N_2$ by molar measure, 1 mole of gas consists of 0.9 mole $O_2$ and 0.1 mole $N_2$. With 10% of the oxygen converted to $O_3$, the emerging gas consists of 0.06 mole $O_3$, 0.81 mole $O_2$, and 0.1 mole $N_2$ for a total of 0.91 mole. The molar percentage $O_2$ is 6.2%. The speed of sound still has a 1-to-1 relationship because each gas has a concentration that is a unique function of the ozone concentration, and hence has a unique speed of sound corresponding to that concentration.

The change in the speed of sound depends upon the change in ozone concentration in a gas. In ozone generation systems, the oxygen content in air is typically increased before the resulting gas is sent to the ozone generation cell. Hence it is good to know the composition of the gas entering the generation cell, as well as after the cells. Air, for example, can be assumed to be 78% $N_2$, 21% $O_2$ and 1% argon. The published speed of sound at 0° C. is respectively 337 m/s, 316 m/s, and 307 m/s through these respective component gasses. By averaging these speeds in proportion to their proportion in air, an overall speed of sound in air is found to be 332 m/s. This compares well to a published speed of 331 m/s. A reasonable estimate for the speed of sound in ozone at 0° C. is 249 m/s, though this is an unlikely direct measurement since high concentrations of ozone are unstable.

The following are illustrative examples with different concentrations of oxygen entering the discharge cell. The first illustration assumes that a sample of gas consisting of 0.8 mole $N_2$ and 0.2 mole $O_2$, an approximation of air. Following the calculations above, the speed of sound in this mixture is 332.80 m/s. If this sample is then passed through an ozone generating cell, some of the $O_2$ is converted to $O_3$ which reduces the total molar quantity of gas. Assuming that 0.1 mole of the $O_2$ is converted to $O_3$, the total output is 0.8 mole $N_2$, 0.1 mole $O_2$, and 0.0667 mole $O_3$, for a total of 0.967 mole. The molar percentage of $O_3$ is 6.9%. The speed of sound in the mixture of gases is 328.65 m/s and the change in speed of sound is −4.146 m/s with the proportional change −0.01245.

In comparison, with the assumption that the sample of gas consists of 1.0 mole $O_2$, i.e., the sample is all oxygen, the speed of sound in this mixture is 316 m/s following the calculations above. If the sample is passed through an ozone generating cell, some of the $O_2$ is converted to $O_3$ to reduce the total molar quantity of gas. Assume, as in the last case, that 0.1 mole of the $O_2$ is converted to $O_3$. The total output is 0.9 mole $O_2$, and 0.0666 mole $O_3$, for a total of 0.967 mole. The molar percentage of $O_3$ is 6.9% as before. The speed of sound in the mixture of gases is 311.28 m/s. The change in speed of sound is −4.720 m/s and the proportional change is −0.01493.

It should be noted that the proportional change of the speed of sound relative to proportion of oxygen in the feed gas entering the cell is greater for pure oxygen than for air. This may be viewed in heuristic fashion. The proportion of nitrogen in the ozone-bearing gas increases, as oxygen is converted to ozone, if there is a lot of nitrogen to begin with. The increased nitrogen, having a relatively high speed of sound, tends to counteract the reduction in the speed of sound due to increasing proportion of ozone.

In returning to the conduit path length L, there should be considered some practical constraints to the length of the conduit as mentioned earlier. These constraints depend on the speed of sound of the gases being measured, the frequency of operation, and the method of measuring or detecting phase shift. For each gas, there is a corresponding speed of sound and a corresponding wavelength. Among the gases there is a gas with a maximum wavelength $\lambda_{max}$ and a gas with a minimum wavelength $\lambda_{min}$. If phase shift is to be limited to 360 degrees, then $L/\lambda_{min} - L/\lambda_{max}$ must be less than 1, i.e.:

$$L/\lambda_{min} - L/\lambda_{max} < 1.$$

This corresponds to the difference in number of wavelengths contained in the conduit is less than 1. By manipulating the terms to determine the conduit length, one obtains:

$$L < \lambda_{min} \cdot \lambda_{max}/(\lambda_{min} - \lambda_{max}).$$

Similarly, if phase shift is to be limited to 180 degrees, then $L/\lambda_{min} - L/\lambda_{max}$ must be less than ½, i.e., $$L/\lambda_{min} - L/\lambda_{max} < \tfrac{1}{2}; \text{ or}$$

$$L < \tfrac{1}{2} \lambda_{min} \cdot \lambda_{max}/(\lambda_{min} - \lambda_{max}) \text{ in this case.}$$

Some exemplary numbers may illustrate these points. With the frequency of the analyzer fixed at 40 KHz, and assuming that the speed of sound of the reference gas (air) $S_{ref}$ is 343 m/s or $\lambda_{ref}=0.858$ cm, and the range of speed of sound of other gases (oxygen—enhanced air and ozone) in the analyzer, $\Delta S$, is 290 m/s, the maximum wavelength $\lambda_{max}$ ($\lambda_{ref}$) is 0.858 cm and the minimum wavelength $\lambda_{min}$ is 0.725 cm. If phase shift is to be limited to 180 degrees, then $L((1/0.725)-(1/0.858)) < \tfrac{1}{2}$, or $L<2.339$ cm. Similarly, if phase shift is to be limited to 360 degrees, then $L<4.677$ cm. These numbers correspond to 2.726 wavelengths of the reference gas ($\lambda_{ref}$) and 5.452 wavelengths of the reference gas ($\lambda_{ref}$) respectively.

But very short conduits cause artifacts due to standing waves, artifacts due to the acoustic contribution of holes for ingress and egress of test gases, artifacts due to the uncertain phase relationship of electrical signals to acoustic signals, and artifacts due to electrical and/or acoustical noise. For these reasons, it is desirable to have a conduit that includes at least 10 wavelengths of sound in the reference gas in order to minimize these artifacts. As described in the previous paragraph, a conventional phase detector places a severe constraint on conduit length. In the case of a 360° phase shift detector, path length L of the conduit in terms of number of wavelengths of the reference gas can be no greater than 5.452, and in the cases of a 180 degree phase shift detector, the path length can be no more 2.726 wavelengths of the reference gas.

However, by the application of the previously described frequency division technique upon the particular phase shift detection method, the constraint on the conduit path length L can be removed and L lengthened. If the frequency is divided by n, n=8 for example, the maximum number of wavelengths and the maximum length L are each multiplied by a factor of n=8. That is, the upper bound for the conduit path length becomes:

$$L < n \lambda_{min} \cdot \lambda_{max}/(\lambda_{min} - \lambda_{max}) \text{ or } L < \tfrac{1}{2} n \lambda_{min} \cdot \lambda_{max}/(\lambda_{min} - \lambda_{max})$$

depending upon whether the phase shift detector is 360 degrees or 180 degrees respectively.

On the other hand, even with the frequency division technique the upper bounds of the conduit path length are not limitless. Long conduits also cause problems which include signal attenuation, high sample volume, and bulky design. It is desirable to limit the conduit length L to about 30 wavelengths, at which point the disadvantages of long path length begin to become severe.

In a preferred embodiment, a length of conduit corresponding to about 23 wavelengths of sound in reference gas ($\lambda_{ref}$) was selected, i.e., L approximately=23*0.858 cm. This creates a situation in which phase shift exceeds the limit of the 180° phase detector selected, but the use of the frequency division technique described maintains the advantages of a relatively long signal path.

The described relatively simple and low-cost gas analyzer measures the concentration of ozone in an ozone generation system with high resolution and precision, and relatively independently of the oxygen concentration in the feed gas and independently of temperature. Additionally, the concentration of oxygen in the gas fed to the ozone generation is precisely measured. This provides an inexpensive and productive way of generating ozone on site and at the time of use.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. An analyzer for one or more gases derived from a first gas of known composition and speed of sound, each derived gas having a concentration of a component changed, the analyzer comprising:

a first transducer, the first transducer driving continuous sound waves responsive to a fixed frequency signal source;

a conduit acoustically connected to the first transducer, the conduit selectively receiving and holding samples of the first gas and one or more derived gases;

a second transducer acoustically connected to the conduit opposite the first transducer, the second transducer receiving sound waves from the first transducer through the conduit and generating second transducer signals responsive to the received sound waves; and a processing unit constructed and arranged to receive fixed frequency signal source signals and the second transducer signals, the processing unit used to determine a relative phase shift between the frequency source signals and second transducer signals for a gas sample in the conduit, the relative phase shift corresponding to a difference of speed of sound in one gas sample relative to another gas sample, the processing unit including circuitry for lowering the frequency of the received fixed frequency source signals and second transducer signals to expand the range of measurement of the relative phase shift.

2. The analyzer of claim 1 wherein the circuitry for lowering the fixed frequency of the frequency source signals and second transducer signals each comprise a frequency divider circuit.

3. The analyzer of claim 2 wherein the frequency divider circuit comprises a digital counter circuit.

4. The analyzer of claim 3 wherein the frequency divider circuit divides by a divisor having a value of a power of 2.

5. The analyzer of claim 3 wherein the digital counter circuit has a baselien value adjusted so that the range of measurement of the phase shift is expanded and the range of calculation of gas composition is increased.

6. The analyzer of claim 4 wherein the frequency divider circuit divides by 8.

7. The analyzer of claim 2 wherein the conduit has a path length L between the first and second transducers wherein L has a removed constraint from the frequency divider circuit of:

$$L < \lambda_{min} \cdot \lambda_{max}/(\lambda_{min} - \lambda_{max}) \text{ or } L < \tfrac{1}{2}\lambda_{min} \cdot \lambda_{max}/(\lambda_{min} - \lambda_{max})$$

depending upon whether the processing unit limits the relative phase shift to 360 degrees or to 180 degrees respectively, where $\lambda_{min}$=minimum wavelength and $\lambda_{max}$=maximum wavelength of the first gas and one or more gases.

8. The analyzer of claim 7 wherein the conduit has a path length L:

$$L < n\lambda_{min} \cdot \lambda_{max}/(\lambda_{min} - \lambda_{max}) \text{ or } L < \tfrac{1}{2}n\lambda_{min} \cdot \lambda_{max}/(\lambda_{min} - \lambda_{max})$$

depending upon whether the processing unit limits the relative phase shift to 360 degrees or to 180 degrees respectively, and n comprises a divisor for the frequency divider circuit.

9. The analyzer of claim 8 wherein the conduit path length L is more than 10 wavelengths of the first gas.

10. The analyzer of claim 9 wherein the conduit path length L is less than 30 wavelengths of the first gas.

11. The analyzer of claim 1 wherein the first gas comprises air.

12. The analyzer of claim 11 wherein a first derived gas comprises air with an increased concentration of oxygen.

13. The analyzer of claim 12 wherein a second derived gas comprises air with an increased concentration of ozone.

14. The analyzer of claim 1 wherein the conduit is maintained at a selected temperature.

15. The analyzer of claim 14 wherein the conduit comprises an ozone-resistant tubing enclosed in an metal block to provide a thermal mass to the conduit.

16. The analyzer of claim 15 wherein the ozone-resistant tubing comprises polytetrafluoroethylene (PTFE) and the metal block comprises aluminum.

17. The analyzer of claim 1 further comprising a calculating unit for determining from the first gas of known composition the speed of sound of the one or more gases derived from the first gas using the measures phase shift values.

18. The analyzer of claim 17 wherein the calculating unit calculates the concentration of the component changed in the sample of the one or more derived gases.

19. The analyzer of claim 17 wherein the calculating unit is constructed and arranged to calculate the composition of a sample of one or more derived gases using the first gas as a reference.

20. The analyzer of claim 18 wherein the concentration of the component changed in the sample of the one or more derived gases is calculated principally from the proportion of the changed component in the sample of the one or more derived gases.

21. The analyzer of claim 20 wherein the proportion of the changed component in the sample of the one or more derives gases is calculated from a ratio having the determined speed of sound of the sample of the one or more derived gases in the numerator and a speed of sound of 100 percent of the changed component in the denominator.

22. The analyzer of claim 20 wherein the calculation of the concentration of the component changed in the sample of the one or more derived gases includes modifying empirical correction factors.

23. The analyzer of claim 1 wherein the analyzer further comprising a controller block having an oscillator constructed and arranged to drive the first transducer.

* * * * *